(12) United States Patent
Aoyama et al.

(10) Patent No.: US 7,033,588 B2
(45) Date of Patent: Apr. 25, 2006

(54) PREVENTIVE AGENT FOR ASCITES IN POULTRY

(75) Inventors: Tomoya Aoyama, Tokyo (JP); Hironori Kubota, Tokyo (JP); Shigeo Takagi, Ooi-machi (JP); Tsuyoshi Minemura, Ooi-machi (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/483,934

(22) PCT Filed: Jul. 17, 2002

(86) PCT No.: PCT/JP02/07251

§ 371 (c)(1),
(2), (4) Date: Apr. 5, 2004

(87) PCT Pub. No.: WO03/007928

PCT Pub. Date: Jan. 30, 2003

(65) Prior Publication Data

US 2004/0156836 A1    Aug. 12, 2004

(30) Foreign Application Priority Data

Jul. 17, 2001    (JP)    ............................... 2001-216545

(51) Int. Cl.
    A61K 38/43    (2006.01)

(52) U.S. Cl. .................................................... 424/94.1

(58) Field of Classification Search ................. 424/94.1
See application file for complete search history.

(56) References Cited

U.S. PATENT DOCUMENTS

| 4,068,003 A | * | 1/1978 | Miyata | ....................... 424/94.1 |
| 6,441,050 B1 | * | 8/2002 | Chopra | ....................... 514/675 |
| 2002/0102301 A1 | * | 8/2002 | Schwarz | ....................... 424/468 |

FOREIGN PATENT DOCUMENTS

| CN | 86 1 00582 A | | 12/1987 |
| JP | 0075032974 | * | 10/1975 |
| JP | 09-187229 | | 7/1997 |
| WO | WO 98/51164 | | 11/1998 |

* cited by examiner

*Primary Examiner*—Herbert J. Lilling
(74) *Attorney, Agent, or Firm*—Knobbe, Martens, Olson & Bear, LLP

(57) ABSTRACT

It is intended to provide a preventive agent for ascites containing coenzyme Q which can sufficiently exert an effect on preventing ascites even when administering in a small dose and within a short period of time, and the preventive agent for ascites which can be effectively administered to poultry using a simple method. Namely, preventive agent for ascites in poultry containing coenzyme Q and a surfactant, wherein the content of the surfactant is in a range of between 0.5 and 80 parts by weight with respect to a total amount of the preventive agent for ascites.

5 Claims, No Drawings

# PREVENTIVE AGENT FOR ASCITES IN POULTRY

RELATED APPLICATIONS

This application is the U.S. National Phase under 35 U.S.C. § 371 of International Application PCT/JP02/07251, filed Jul. 17, 2002, which was published in a language other than English which claims priority of Japanese Patent Application No. 2001-216545, filed Jul. 17, 2001 Each of the above applications are incorporated herein by reference in their entirety.

TECHNICAL FIELD

The present invention relates to a preventive agent for ascites (also referred to as "preventive" in the present invention) in poultry (particularly intended for broilers, the chickens), a method of preventing ascites in poultry using the preventive agent for ascites, and a method of improving a rate of raising of poultry using the preventive agent for ascites.

The present invention is useful for feed, feed additives, and drugs for animals.

BACKGROUND ART

Preventing ascites in poultry, improving a rate of raising, and preventing the ascites while maintaining a high growth rate of broilers are important issues for productivity of poultry.

Up to now, coenzyme Q is known to prevent the ascites in the broilers (JP 06-287136 A, JP 07-123928 A). In addition, administering of the coenzyme Q with an antioxidant, an antacid, an ammonia generation inhibitor, or the like to the broilers is also known (JP 09-187229 A).

Further, regarding the time and the period of administering the coenzyme Q, PCT publication WO98/51164A discloses administering for 7 days or longer to the broilers between 10 days and 35 days in age.

However, a conventional preventive containing coenzyme Q was unsatisfactory in terms of exerting an effect with a small dose. Further, the preventive was also unsatisfactory in terms of exerting an effect within a short period of administering.

The Coenzyme Q is fat-soluble and has a property of not dispersing easily in water. Therefore, by administering a preventive agent for ascites containing coenzyme Q using a conventional administration method, in other words, by only dispersing in water, the preventive floats on water surface and cannot be administered accurately. Further, by mixing to adsorb the preventive to powder or by dissolving in oil and then dispersing in water, the preventive floats on water surface or precipitates. Therefore, sufficient and accurate administering of the preventive agent for ascites containing coenzyme Q was impossible. Further, much of the water quality of water used in a poultry farm is high in hardness or contains a disinfectant added, and a problem exists in which dispersing the coenzyme Q is difficult, so effective administering has been more difficult.

In other words, with regard to a preventive agent for ascites containing coenzyme Q, a conventional technology is insufficient and there is more need for study, considering an amount of use and period of use and considering accurate and simple administering.

DISCLOSURE OF THE INVENTION

The present invention has been made in view of the above-mentioned circumstances, and it is an object of the present invention to provide a preventive agent for ascites containing coenzyme Q, which can sufficiently exert an effect on preventing ascites even when administering in a small dose and within a short period of time.

In addition, it is still an object of the present invention to provide a preventive agent for ascites which can be effectively administered to poultry using a simple method.

The inventors of the present invention, by vigorous research to solve the problem described above, have found out that by using specific ingredients and defining contents of the ingredients, a preventive agent for ascites containing coenzyme Q can be uniformly dispersed without unevenness when dispersed in water, so the coenzyme Q can be accurately and assuredly administered to poultry, thereby completing the invention.

In other words, the present inventions are as described below.

(1) A preventive agent for ascites in poultry comprising coenzyme Q and a surfactant, wherein a content of the surfactant is in a range of between 0.5 and 80 parts by weight with respect to a total amount of the preventive agent for ascites.

(2) A preventive agent for ascites in poultry comprising coenzyme Q, a surfactant, and water, wherein a content of the surfactant is in a range of between 0.5 and 80 parts by weight with respect to a total amount of the preventive agent for ascites.

(3) The preventive agent for ascites in poultry according to the item (1) or (2), wherein a content of the coenzyme Q is 0.5 to 40 parts by weight with respect to a total amount of the preventive agent for ascites.

(4) The preventive agent for ascites in poultry according to any one of the items (1) to (3), wherein an average particle size of an oil-in-water type emulsion is 15 μm or smaller in particle size when forming the oil-in-water type emulsion by dispersing the preventive agent for ascites in poultry in water, and/or diluting the preventive agent for ascites in poultry with water.

(5) A method of preventing ascites in poultry, comprising administering the preventive agent for ascites in poultry according to any one of the items (1) to (4) to thereby prevent the ascites in poultry.

(6) A method of improving a rate of raising of poultry, comprising administering the preventive agent for ascites in poultry according to any one of the items (1) to (4) to thereby improve a rate of raising of poultry.

Hereinafter, the present invention is described in detail.

<1> Preventive Agent for Ascites of the Present Invention

A preventive agent for ascites of the present invention comprises coenzyme Q and a surfactant.

The surfactant of the present invention can be suitably selected from surfactants generally used. Among them, a nonionic surfactant is preferable, and examples thereof include sorbitan fatty acid ester, polyoxyethylene fatty acid ester, polyoxyethylene sorbitan fatty acid ester, polyalcohol fatty acid ester, glycerin fatty acid ester, and polyglycerin fatty acid ester.

The surfactant is contained in a specific amount, that is, 0.5 to 80 parts by weight, preferably 10 to 60 parts by weight with respect to a total amount of preventive agent for ascites. If a content of the surfactant is less than 0.5 parts by weight with respect to the total amount of the preventive agent for ascites, dispersion of a coenzyme may not be uniform when dispersing in water during use. On the other hand, if the content of the surfactant exceeds 80 parts by weight with respect to the total amount of the preventive, the dispersibility of the coenzyme in water remains the same compared to a case of 80 parts by weight.

In addition, water may be further added to the composition described above to prepare a preventive agent for ascites in poultry, because, a form of a solution or an emulsion is used generally. In this case, the surfactant is contained in 0.5 to 80 parts by weight, preferably 10 to 60 parts by weight with respect to the total amount of the preventive agent for ascites. If the content of the surfactant is less than 0.5 parts by weight with respect to the total amount of the preventive agent for ascites, the dispersion of the coenzyme may not be uniform when dispersing in water during use. On the other hand, if the content of the surfactant exceeds 80 parts by weight with respect to the total amount of the preventive, the dispersibility of the coenzyme in water remains the same compared to a case of 80 parts by weight.

The coenzyme Q used in the present invention is coenzymes $Q_6$ to $Q_{12}$, preferably $Q_9$ and $Q_{10}$.

Further, the content of coenzyme Q in the present invention is generally 0.5 to 40 parts by weight, preferably 0.5 to 30 parts by weight, more preferably 1 to 20 parts by weight with respect to the total amount of the preventive agent for ascites. If the content of coenzyme Q is less than 0.5 parts by weight with respect to the total amount of the preventive agent for ascites, an effect for preventing ascites in poultry itself may not be expressed, or the effect may be significantly decreased. On the other hand, if the content exceeds 40 parts by weight with respect to the total amount of the preventive, an exertion of a higher preventing effect compared to 40 parts by weight cannot be expected.

When forming an oil-in-water type emulsion by dispersing the preventive agent for ascites in poultry prepared as described above in water, and/or by diluting the preventive agent for ascites in poultry with water, an average particle size of the oil-in-water type emulsion is 15 µm or smaller, more preferably 5 µm or smaller. In this case, if the average particle size is 15 µm or larger, an emulsion might not form and may settle in water. Stable dispersibility in water can be secured by existence of such an emulsion in water.

The preventive agent for ascites of the present invention can be contained various ingredients other than the ingredients described above.

For example, as an agent promoting dissolution of the coenzyme, fats and oils can be added as required. As the fats and oils of the present invention, natural animal and vegetable oils or the like can be used, and examples thereof include soybean oil, cottonseed oil, groundnut oil, safflower oil, olive oil, cacao butter, wheat germ oil, whale wax, beeswax, mono, di, and tri esters of fatty acids having 4 to 18 carbon atoms, and their mixtures. In addition, similar to the fats and oils described above, hydrocarbon oils such as liquid paraffin can be also used to fulfill a similar role.

Further, a carrier consisting of powders of lactose, cornstarch, crystalline cellulose, or saccharose can also be contained.

Further, to prepare the preventive into a powder form, an auxiliary agent such as wheat starch, dextrin, hydroxypropyl starch, carmellose calcium, and carmellose sodium can be contained.

Further, other additives can be added, and examples of additives generally used that can be added other than the ones described above include, an excipient; an edulcorant; and a fragrance; such as potato starch, D-mannitol, sorbitol, acacia gum, gelatin, light silicic anhydride, agar, carrageenan, ethyl cellulose, fructose, hydrated silicon dioxide, glucose, citric acid, tartaric acid, carmellose, CMC-Ca, reduced maltose, sodium hydrogen carbonate, sodium carbonate, magnesium bicarbonate, magnesium carbonate, calcium carbonate, ascorbic acid, succinic acid, adipic acid, fumaric acid, tartaric acid, malonic acid, and malic acid.

Further, polyalcohol such as polyethylene glycol, propylene glycol, glycerin, and sorbitol may optionally be contained as required.

Further, pharmaceuticals, galenicals, or the like used as nonprescription drugs such as a fat-soluble drug, and a water-soluble drug may also be contained.

Each of the compounding ingredients described above can be suitably and arbitrary used in combination of two or more thereof.

As a form of the preventive agent for ascites in poultry, coenzyme Q and a surfactant may be dissolved, the polyalcohol described above such as glycerin may be added as required, and then the thus-obtained solution can be retained on a carrier.

The preventive of the present invention may be in any forms of powder, particulate, and liquid, and more specifically, any forms such as tablet, granule, capsule, and solution may be adopted.

When using the thus-obtained preventive agent for ascites in poultry to poultry, if a preparation is powder or particulate, it may be actively dissolved in water. On the other hand, if the preparation is a solution, it can be mixed as it is in water for use. In either case, a preventive with a composition of the present invention can be uniformly dispersed when mixed in water, does not float on water surface, and does not crystallize or precipitate, thereby attaining a state of retaining excellent dispersibility.

<2> Method of Preventing Ascites and Method of Improving a Rate of Raising of the Present Invention Ascites in poultry can be prevented by administering the preventive agent for ascites in poultry of the present invention to poultry. In addition, the preventive prevents ascites, consequently preventing sudden death syndrome effectively, thereby allowing an improvement of a rate of raising.

In the method of preventing ascites and the method of improving a rate of raising of the present invention, the target poultry to which those methods are adopted is particularly boiler, which is chicken. However, quail, turkey, ostrich, duck, laying hen, parent stocks thereof, or the like may be included. Further, a kind of chicken is not particularly limited, if the poultry refers to broilers.

In the methods described above, peroral administration is preferable as a method of administering the preventive agent for ascites to the poultry. In particular, the preventive of the present invention excels in dispersibility in water, thus can be administered as it is in drinking water of poultry.

As described above, it is a feature of the method using the preventive of the present invention, in which the preventive of the present invention can be administered accurately and assuredly through a simple method as administering in drinking water.

When administering in drinking water as described, the preventive of the present invention effectively functions even in the presence of chlorine compounds as a disinfectant or antibiotics for treating infectious diseases in the drinking water.

As a number of days of administration of the preventive used in the method described above, a sufficient effect is apparent with administering by adding to drinking water once a day for 1 to 6 days, for example. However, using the preventive of the present invention, an effect for sufficiently preventing ascites is apparent even with 1 to 4 days of administration, and also with 2 to 3 days of administration.

As a time of administration, it is necessary to administer the preventive 14 days or longer before the shipping date, but administering the preventive 20 to 30 days before the shipping date enables considerable decrease in mortality rate by ascites.

Further, as a dose, for example, administration with a dose of 0.01 to 20 mg/kg-weight per day, preferably 2 to 10 mg/kg-weight enables effective prevention of ascites.

The preventive of the present invention effectively functions in use under general raising conditions but also effectively functions in use under a raising condition in which feed energy is increased to 3,150 calories/kg or higher to accelerate the growth rate.

BEST MODE FOR CARRYING OUT THE INVENTION

Hereinafter, the present invention is more specifically described by way of examples.

EXAMPLE 1

Production of a Preventive Agent for Ascites and Evaluation of the Preventive

Ubidecarenone, glyceryl monostearate (MGS-150, available from Nikko Chemicals Co., Ltd.) as a surfactant, and soybean oil (available from Yoshida Pharmaceuticals Co., Ltd.) as fats and oils were mixed in a ratio shown in Table 1 described below and heated to about 60° C. to dissolve.

Then, purified water was added to the mixture under stirring, and an emulsion liquid was obtained using Agi Homo Mixer (manufactured by Tokushu Kika Kogyo Co., Ltd.) (Example Prescription 1, Comparative Example Prescription 1).

The same method described above was repeated except that the surfactant described above was changed to decaglycerin fatty ester (DG5-0, available from Nikko 5 Chemicals Co., Ltd.) and a blending ratio was changed to obtain an emulsion liquid (Example Prescription 2, Comparative Example Prescription 2). Each of the comparative prescriptions has a lower content of surfactants compared to those of example prescriptions. Values of Table 1 are shown in parts by weight.

TABLE 1

| Component | Comparative Example Prescription 1 | Example Prescription 1 | Comparative Example Prescription 2 | Example Prescription 2 |
|---|---|---|---|---|
| Ubi-decarenone | 1 | 1 | 5 | 5 |
| Surfactant | 0.3 | 20 | 0.3 | 35 |
| Soybean oil | 8.7 | 30 | 11.7 | 20 |
| Purified water | 90 | 49 | 83 | 40 |
| Total | 100.0 | 100.0 | 100.0 | 100.0 |

An average particle size of an oil-in-water type emulsion of the thus-prepared emulsion liquid was measured.

The measurement was performed using a laser diffraction particle size analyzer (Microtrac, manufactured by Nikkiso Co., Ltd.). The results are shown in Table 2.

TABLE 2

| Component | Comparative Example Prescription 1 | Example Prescription 1 | Comparative Example Prescription 2 | Example Prescription 2 |
|---|---|---|---|---|
| Average particle size (μm) | 18.6 | 1.08 | 19.3 | 1.95 |

Next, dispersibility of the thus-prepared emulsion liquid in drinking water was evaluated.

The dispersibility of the preventive in water was evaluated by measuring the intensity of the back-scattered light using Turbiscan MA2000, manufactured by Eko Instruments Co., Ltd. A dispersion liquid was poured in a test tube, and the intensity at the middle of the test tube was measured over time. The results are shown in Table 3.

TABLE 3

| | Comparative Example Prescription 1 | Example Prescription 1 | Comparative Example Prescription 2 | Example Prescription 2 |
|---|---|---|---|---|
| Intensity of back-scattered light (%) | | | | |
| 3 hours after start of experiment | 5.6 | 3.2 | 6.1 | 3.9 |
| 6 hours after start of experiment | 12.1 | 4.7 | 16.9 | 4.3 |
| 12 hours after start of experiment | 29.4 | 5.1 | 36.4 | 4.8 |

From the results of Table 3, intensities of scattering light in water of the preventive agent for ascites according to Example Prescription 1 and Example Prescription 2 were substantially constant, and variation with time was not observed. On the other hand, it was confirmed that precipitation of particles or separation occurred in Comparative Example Prescription 1 and Comparative Example Prescription 2.

EXAMPLE 2

Use of the Preventive Agent for Ascites

The preventive agent for ascites obtained in Comparative Example Prescription 1 or Example Prescription 1 was added to the drinking water for administration following the schedule shown in Table 4. 700 chickens per herd of new born broilers (kind of chicken: male Arbor Acre, weight of newborn; 40 g) were raised by floor feeding until 56 days of age. The broilers had free access to the feed and the drinking water. Employed as the raising conditions were heating using floor heating from 0 to 14 days of age (windowless poultry house, 37 to 20° C.), lighting for 24 h, and raising density of 16 chikens/m², without heating from 15 to 56 days of age (open window poultry house, 20 to 5° C.)

The broilers were raised under the respective conditions described above, and causes of death of the broilers which died during raising were investigated. The number of broilers died from ascites was summed. The results are shown in Table 4.

TABLE 4

| Administered formulation | Administering days of age (days) | Dose (mg/day/chicken) (mg co-enzyme Q/day/chicken) | Average shipping weight (kg) | Death rate by ascites (%) |
|---|---|---|---|---|
| Example Prescription 1 | 38, 39, 40 | 1,000 (10) | 2,900 | 3.6 |
| Comparative Example Prescription 1 | 38, 39, 40 | 1,000 (10) | 2,900 | 7.6 |

EXAMPLE 3

Confirmation of Shortening Effect on Administration of the Preventive Agent for Ascites The preventive agent for ascites obtained in Comparative Example Prescription 2 or Example Prescription 2 was added to the drinking water for administration following the schedule shown in Table 5. 700 chickens per herd of new born broilers (kind of chicken: male Arbor Acre, weight of newborn: 40 g) were raised by floor feeding until 56 days of age. The broilers had free access to the feed and the drinking water. Employed as the raising conditions were heating using floor heating from 0 to 14 days of age (windowless poultry house, 37 to 20° C.), lighting for 24 h, and raising density of 16 chikens/m², without heating from 15 to 56 days of age (open window poultry house, 20 to As a comparative control, a herd to which the coenzyme Q was not administered was raised under the same condition as the condition described above.

The broilers were raised under the respective conditions described above, and causes of death of the broilers which died during raising were investigated. The number of broilers died from ascites was summed. The results are shown in Table 5.

TABLE 5

| Administered formulation | Administering days of age (days) | Dose (mg/day/chicken) (mg coenzyme Q/day/chicken) | Death rate by ascites (%) |
|---|---|---|---|
| Coenzyme not administered | — | 0 (0) | 12.8 |
| Example Prescription 2 | 40 | 480 (24) | 8.2 |
|  | 37, 38, 39, 40 | 120 (6) | 6.3 |
|  | 35, 36, 37, 38, 39, 40 | 80 (4) | 6.1 |
| Comparative Example Prescription 2 | 40 | 480 (24) | 12.2 |
|  | 37, 38, 39, 40 | 120 (6) | 11.8 |
|  | 35, 36, 37, 38, 39, 40 | 80 (4) | 11.7 |
|  | 33, 34, 35, 36, 37, 38, 39, 40 | 60 (3) | 7.4 |

It could be confirmed that the number of days of administration can be shortened to 6 days or less using the preventive agent for ascites of the present invention.

EXAMPLE 4

Confirmation of Dose-Reducing Effect on Administration of the Preventive Agent for Ascites The preventive agent for ascites obtained in Comparative Example Prescription 2 or Example Prescription 2 was added to the drinking water for administration following the schedule shown in Table 6. 700 chickens per herd of new born broilers (kind of chicken: male Cobb, weight of newborn: 42 g) were raised by floor feeding until 56 days of age. The broilers had free access to the feed and the drinking water. Employed as the raising conditions were heating using floor heating from 0 to 14 days of age (windowless poultry house, 37 to 20° C.), lighting for 24 h, and raising density of 16 chikens/m², without heating from 15 to 56 days of age (open window poultry house, 20 to 5° C.).

As a comparative control, a herd to which the coenzyme Q was not administered was raised under the same condition as the condition described above.

The broilers were raised under the respective conditions described above, and causes of death of the broilers which died during raising were investigated. The number of broilers died from ascites was summed. The results are shown in Table 6.

TABLE 6

| Administered formulation | Dose (mg/day/chicken) (mg coenzyme Q/day/chicken) | Administering days of age (days) | Death rate by ascites (%) |
|---|---|---|---|
| Coenzyme not administered | — | — | 14.8 |
| Example Prescription 2 | 1 (0.05) | 33, 34, 35, 36, 37, 38, 39, 40 | 9.8 |
|  | 3 (0.15) | 33, 34, 35, 36, 37, 38, 39, 40 | 7.5 |
|  | 9 (0.45) | 33, 34, 35, 36, 37, 38, 39, 40 | 5.8 |
| Comparative Example Prescription 2 | 1 (0.05) | 33, 34, 35, 36, 37, 38, 39, 40 | 12.5 |
|  | 3 (0.15) | 33, 34, 35, 36, 37, 38, 39, 40 | 10.2 |
|  | 9 (0.45) | 33, 34, 35, 36, 37, 38, 39, 40 | 7.9 |

It could be confirmed that the dose can be reduced from ½ to ⅓ using the preventive agent for ascites of the present invention.

INDUSTRIAL APPLICABILITY

According to the present invention, the preventive agent for ascites can be uniformly dispersed in water, so the preventive can be accurately administered to poultry. In particular, the preventive agent for ascites in can be effectively administered to the poultry through a simple method in which the preventive of the present invention can be directly mixed to a drink of the poultry. In addition, the preventive of the present invention can sufficiently exert an effect on preventing ascites in poultry even in administering in a small dose and within a short period of time. Further, an effect of enabling significant shortening of administering period, in particular, allows taking effective actions even if the ascites cannot be predicted, by keeping the damage of ascites in poultry to a minimum by administering the preventive immediately after the symptoms develop.

What is claimed is:

1. A preventive agent for ascites in poultry comprising coenzyme Q, a surfactant, and water, wherein a content of the surfactant is in a range of between 10 and 60 parts by weight with respect to 100 parts by weight of a total amount of the preventive agent for ascites, wherein an average particle size of an oil-in-water type emulsion formed in the preventive agent for ascites in poultry is 15 μm or smaller in particle size.

2. A method of preventing ascites in poultry, comprising administering a preventive agent for ascites in poultry which comprises coenzyme Q and a surfactant, wherein a content of the surfactant is in a range of between 0.5 and 80 parts by weight with respect to 100 parts by weight of a total amount of the preventive agent for ascites.

3. A method of improving a rate of raising of poultry, comprising administering a preventive agent for ascites in poultry which comprises coenzyme Q and a surfactant, wherein a content of the surfactant is in a range of between 0.5 and 80 parts by weight with respect to 100 parts by weight of a total amount of the preventive agent for ascites.

4. A method of preventing ascites in poultry, comprising administering a preventive agent for ascites in poultry which comprises coenzyme Q, a surfactant, and water, wherein a content of the surfactant is in a range of between 0.5 and 80 parts by weight with respect to 100 parts by weight of a total amount of the preventive agent for ascites.

5. A method of improving a rate of raising of poultry, comprising administering a preventive agent for ascites in poultry which comprises coenzyme Q, a surfactant, and water, wherein a content of the surfactant is in a range of between 0.5 and 80 parts by weight with respect to 100 parts by weight of a total amount of the preventive agent for ascites.

* * * * *

UNITED STATES PATENT AND TRADEMARK OFFICE
CERTIFICATE OF CORRECTION

PATENT NO. : 7,033,588 B2 Page 1 of 1
APPLICATION NO. : 10/483934
DATED : April 25, 2006
INVENTOR(S) : Aoyama et al.

It is certified that error appears in the above-identified patent and that said Letters Patent is hereby corrected as shown below:

Column 3, Line 2, "S dispersing in water" should be changed to --dispersing in water--

Column 6, Line 43-44, "from Nikko 5 Chemicals" should be changed to --from Nikko Chemicals--

Column 7, Line 1 "16 chikens/m$^2$," should be changed to --16 chickens/m$^2$,--

Column 7, Line 39, "of 16 chikens/m$^2$," should be changed to --16 chickens/m$^2$,--

Column 7, Line 40, "house, 20 to" should be changed to --house, 20 to 5° C.).--

Column 8, Line 20, "of 16 chikens/m$^2$," should be changed to --16 chickens/m$^2$,--

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,033,588 B2 |
| APPLICATION NO. | : 10/483934 |
| DATED | : April 25, 2006 |
| INVENTOR(S) | : Aoyama et al. |

It is certified that error appears in the above-identified patent and that said Letters Patent is hereby corrected as shown below:

Column 5, Line 43-44, "from Nikko 5 Chemicals" should be changed to --from Nikko Chemicals--

Signed and Sealed this

Thirtieth Day of January, 2007

JON W. DUDAS
*Director of the United States Patent and Trademark Office*